(12) United States Patent
Atanasoska et al.

(10) Patent No.: US 8,386,031 B2
(45) Date of Patent: Feb. 26, 2013

(54) IMPLANTABLE SELF-POWERED BIODEGRADABLE MEDICAL DEVICE TO TREAT OR PREVENT REPERFUSION INJURY

(75) Inventors: Liliana Atanasoska, Edina, MN (US); Aiden Flanagan, Galway (IE); Liza J. Davis, St. Michael, MN (US); Kent Harrison, Maple Grove, MN (US); David J. Sogard, Edina, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 122 days.

(21) Appl. No.: 12/826,030

(22) Filed: Jun. 29, 2010

(65) Prior Publication Data
US 2010/0331775 A1 Dec. 30, 2010

Related U.S. Application Data

(60) Provisional application No. 61/222,027, filed on Jun. 30, 2009.

(51) Int. Cl.
*A61N 1/30* (2006.01)
*A61M 31/00* (2006.01)
(52) U.S. Cl. .......................... 604/20; 604/501
(58) Field of Classification Search ............... 604/890.1, 604/891.1, 892.1, 264, 93.01, 20
See application file for complete search history.

(56) References Cited

U.S. PATENT DOCUMENTS

| | | | |
|---|---|---|---|
| 4,642,230 A * | 2/1987 | Whitehead et al. ........... | 424/409 |
| 4,747,819 A | 5/1988 | Phipps et al. | |
| 5,711,761 A | 1/1998 | Untereker et al. | |
| 5,741,224 A * | 4/1998 | Milder et al. ................. | 604/20 |
| 5,759,564 A * | 6/1998 | Milder et al. ................. | 424/426 |
| 5,935,598 A | 8/1999 | Sage et al. | |
| 6,030,358 A * | 2/2000 | Odland ......................... | 604/27 |
| 6,712,802 B1 | 3/2004 | Cairns et al. | |
| 2003/0028170 A1 | 2/2003 | Anderson et al. | |
| 2004/0106841 A1 | 6/2004 | Shaw et al. | |
| 2004/0253304 A1 | 12/2004 | Gross et al. | |
| 2005/0267565 A1 | 12/2005 | Dave et al. | |
| 2006/0052768 A1* | 3/2006 | Joshi et al. ................. | 604/892.1 |
| 2006/0093923 A1 | 5/2006 | Howard et al. | |
| 2006/0184092 A1 | 8/2006 | Atanasoska et al. | |

(Continued)

FOREIGN PATENT DOCUMENTS

EP 0 612 520 A2 8/1994
WO 2004/066903 A1 8/2004

(Continued)

OTHER PUBLICATIONS

Apaydin et al., The Effects on Myocardial Improvement using ATP-MgCl2 during the Ischemia Reperfusion Period; an in Vitro Study, Turk. J. Vet. Anim. Sci., 30 (2006), pp. 449-456, TÜBİTAK.

(Continued)

*Primary Examiner* — Victoria P Shumate
(74) *Attorney, Agent, or Firm* — Kenyon & Kenyon LLP

(57) ABSTRACT

In one embodiment, the present disclosure provides a biodegradable, self-powered medical device for preventing or reducing reperfusion injury, comprising a galvanic cell, the galvanic cell comprising: a first biodegradable electrode member; and a second biodegradable electrode member comprising a biodegradable conductive polymer and an electrode-releasable therapeutic agent, wherein the galvanic cell generates an electric force sufficient to cause the electrode-releasable therapeutic agent to be released from the biodegradable conductive polymer and elute to a target location. The device may further include a reservoir material containing a burst-release therapeutic agent.

20 Claims, 1 Drawing Sheet

U.S. PATENT DOCUMENTS

| | | | |
|---|---|---|---|
| 2006/0233712 A1 | 10/2006 | Penades et al. | |
| 2007/0060862 A1 | 3/2007 | Sun et al. | |
| 2008/0058701 A1 | 3/2008 | Smith | |
| 2008/0086072 A1 | 4/2008 | Bonutti et al. | |
| 2008/0275430 A1* | 11/2008 | Belsky et al. | 604/890.1 |
| 2009/0048556 A1 | 2/2009 | Durand | |

FOREIGN PATENT DOCUMENTS

WO        2006/086672 A1      8/2006

OTHER PUBLICATIONS

Atanasoska et al., XPS Studies on Conducting Polymers: Polypyrrole Films Doped with Perchlorate and Polymeric Anions, Chem. Mater., 4 (5) (1992), pp. 988-994, American Chemical Society.

Ateh et al., Polypyrrole-based conducting polymers and interactions with biological tissues, Journal of the Royal Society Interface, 3 (Published online Jun. 22, 2006), pp. 741-752, the Royal Society.

Bolzan et al., Electrochemical study of thiourea and substituted thiourea adsorbates on polycrystalline platinum electrodes in aqueous sulfuric acid, Journal of Applied Electrochemistry, 32 (2002), pp. 611-620, Kluwer Academic Publisher.

Bruno et al., Biomimetic Synthesis of Water Soluble Conductive Polypyrrole and Poly (3,4 ethylenedioxythiophene), Materials Research Society Symp. Proc., 736 (2003), pp. D7.13.1-6, Materials Research Society.

Carrea et al., Reduction of canine myocardial infarct size by a diffusible reactive oxygen metabolite scavenger. Efficacy of dimethylthiourea given at the onset of reperfusion, Journal of the American Heart Association Circulation Research, 68 (1991), pp. 1652-1659, the American Heart Association.

Chen et al., Hydrothermal synthesis of cathode materials, Journal of Power Sources, 174 (2007) pp. 442-448, Elsevier.

Chen et al., The hydrothermal synthesis and characterization of olivines and related compounds for electrochemical applications, Solid State Ionics, 178 (2008) pp. 1676-1693, Elsevier.

Fonseca et al., Development of a biodegradable polymer electrolyte for rechargeable batteries, Journal of Power Sources, 155 (2006) pp. 381-384, Elsevier.

Gao et al., Enhancement of Glutathione Cardioprotection by Ascorbic Acid in Myocardial Reperfusion Injury, The Journal of Pharmacology and Experimental Therapeutics, 301 (2) (2002), pp. 543-550, the American Society for Pharmacology and Experimental Therapeutics.

Garcia et al. Magnesium reduces free radicals in an in vivo coronary occlusion-reperfusion model, Journal of the American College of Cardiology, 32 (1998), pp. 536-539, Elsevier Science, Inc.

Greca et al., The protective effect of methylene blue in lungs, small bowel and kidney after intestinal ischemia and reperfusion, Acta Cirurgica Brasileira, 23(2) (2008), pp. 149-156.

Guimard et al., Conducting polymers in biomedical engineering, Progress in Polymer Science, 32, (2007) pp. 876-921, Elsevier.

Johnson et al., A Pulsed Electric Field Enhances Cutaneous Delivery of Methylene Blue in Excised Full-Thickness Porcine Skin, The Journal of Investigative Dermatology, 111(3) (1998), pp. 457-463, the Society for Investigative Dermatology, Inc.

Li et al., Controlled release of heparin from polypyrrole-poly (vinyl alcohol) assembly by electrical stimulation, Wiley InterScience, J. Biomed. Mater. Res. 73A (2005), pp. 171-181, Wiley periodicals, Inc.

Morita et al., Rechargeable Magnesium Batteries Using a Novel Polymeric Solid Electrolyte, Electrochemical and Solid-State Letters, 4 (11) (2001), pp. A177-A179, the Electrochemical Society, Inc.

Moulton et al., Galvanic coupling conducting polymers to biodegradable Mg initiates autonomously powered drug release, Journal of Materials Chemistry, 18 (2008), pp. 3608-3613, the Royal Society of Chemistry.

Nair et al., Biodegradable polymers as biomaterials, Progress in Polymer Science, 32 (2007) pp. 762-798, Elsevier.

Gizdavic-Nikolaidis et al., Conducting polymers as free radical scavengers, Synthetic Metals, 140 (2004), pp. 225-232, Elsevier.

Purushothaman et al., Reducing Mass-Transport Limitations by Application of Special Pulsed Current Modes, Journal of the Electrochemical Society, 152 (4) (2005), pp. J33-J39, the Electrochemical Society.

Rivers et al., Synthesis of a Novel, Biodegradable Electrically Conducting Polymer for Biomedical Applications, Advanced Functional Materials, 12 (1) (2002), pp. 33-37, Wiley VCH Verlag GmbH.

Saritas et al., Effects of ATP-MgCl2 on Myocardial Ischemia-Reperfusion Injury: An in Vivo Experimental Study, Turk. J. Vet. Anim. Sci., 30 (2006), pp. 471-475, TÜBİTAK.

Sono, The Roles of Superoxide Anion and Methylene Blue in the Reductive Activation of Indoleamine 2,3-Dioxygenase by Ascorbic Acid or by Xanthine Oxidase-Hypoxanthine, The Journal of Biological Chemistry, 264 (3), Issue of Jan. 25, 1989, pp. 1616-1622, the American Society for Biochemistry and Molecular Biology, Inc.

Wan et al., Preparation and characterization of porous conducting poly (DL-lactide) composite membranes, Journal of Membrane Science, 246 (2005), pp. 193-201, Elsevier.

Wang et al., A biodegradable electrical bioconductor made of polypyrrole nanoparticle/poly(D,L-lactide) composite: A preliminary in vitro biostability study, Journal of Biomedical Materials Research, 66A (2003), pp. 738-746, Wiley Periodicals, Inc.

Yoshida et al., High Ionic Conducting Polymer with Polysaccharide and its Applications, Fujitsu Sci. Tech. Journal, 38 (1) ( Jun. 2002), pp. 39-45.

Yue et al., Ion conducting behaviour and morphology of solid polymer electrolytes based on a regioselectively substituted cellulose ether with PEO side chains, Journal of Materials Chemistry, 12 (2002), pp. 2281-2285, the Royal Science of Chemistry.

Scheiner et al., Imbalanced Biphasic Electrical Stimulation: Muscle Tissue Damage, Annals of Biomedical Engineering, vol. 18 (4) pp. 407-425 (Jul. 1990).

Fonseca et al., Thermal and Conduction Properties of a PCL-biodegradable Gel Polymer Electrolyte with LiClO4, LiF3CS03, and LiBF4 Salts, International Journal of Electrochemical Science, vol. 2 (2007), pp. 52-63.

Nimma et al., Preparation and Characterization of PVC/PMMA Blend Polymer Electrolytes Complexed with LiN (C2F5S02)2, Ciência e Tecnologia, vol. 14, n° 1 (2004), pp. 1-7.

Paoli et al., Electrochemistry, Polymers and Opto-Electronic Devices: A Combination with a Future, J. Braz. Chem. Soc., vol. 13, No. 4 (2002), pp. 410-424.

Schewendeman et al., Model Features of a Cardiac Iontophoretic Drug Delivery Implant, Pharmaceutical Research, 12 (5) (1995), pp. 790-795, Plemum Publishing Corporation.

Wu et al., Nanostructured Iron Oxide Films Prepared by Electrochemical Method for Electrochemical Capacitors, Electrochemical and Solid-State Letters, 12 (1), pp. A1-A4, 2009, the Electrochemical Society.

Ito et al., Lithium battery having a large capacity using Fe3O4 as a cathode material, Journal of Power Sources, 146, (2005), pp. 319-322, Elsevier.

Winther-Jensen et al., Control of magnesium interfacial reactions in aqueous electrolytes towards a biocompatible battery, Electrochimica Acta, 53, (2008), pp. 5881-5884, Elsevier.

Kona, Circuitry for a Remotely Powered Bioimplantable Gastric Electrical Stimulation System, A Thesis Submitted to the Graduate Faculty of the Louisiana State University and Agricultural and Mechanical College, Dec. 2003.

Carbunaru et al., Rechargeable Battery-Powered bion® Microstimulators for Neuromodulation, Proceedings of the 26th Annual International Conference of the IEEE EMBS, San Francisco, CA, USA, Sep. 1-5, 2004.

Thünemann et al., Complexes of Poly(ethylene oxide)-block-Poly(L-glutamate) and Diminazene, Langmuir, 22 (5) (2006), pp. 2323-2328, the American Chemical Society.

Rekha et al., Pullulan as a Promising Biomaterial for Biomedical Applications: A Perspective, Trends Biomater. Artif. Organs, 20 (2) (2007).

James et al., Polyurethanes with radiopaque properties, Biomaterials, 27 (2006), pp. 160-166, Elsevier.

Peuster et al., Long-term biocompatibility of a corrodible peripheral iron stent in the porcine descending aorta, Biomaterials, 27 (2006), pp. 4955-4962, Elsevier.

Nottelet et al., Synthesis of an X-ray opaque biodegradable copolyester by chemical modification of poly (e-caprolactone), Biomaterials, 27 (2006), pp. 4948-4954, Elsevier.

Guo et al., Investigation of corrosion behaviors of Mg—6Gd—3Y—0.4Zr alloy in NaCl aqueous solutions, Electrochimica Acta, 52 (2007), pp. 2570-2579, Elsevier.

Lv et al., Controlled synthesis of magnesium hydroxide nanoparticles with different morphological structures and related properties in flame retardant ethylene—vinyl acetate blends, Nanotechnology, 15 (2004), pp. 1576-1581, Institute of Physics Publishing.

Yang et al., Solution phase synthesis of magnesium hydroxide sulfate hydrate nanoribbons, Nanotechnology, 15 (2004), pp. 1625-1627, Institute of Physics Publishing.

Mobedi et al., Studying the Degradation of Poly(L-lactide) in Presence of Magnesium Hydroxide, Iranian Polymer Journal, vol. 15, No. 1 (Jan. 2006), pp. 31-39.

International Search Report and the Written Opinion of the International Searching Authority from related International Application No. PCT/US2010/040362, mailed Nov. 19, 2010.

"Batteries Now Implanted," The New Scientist, vol. 200, No. 2684, p. 27 (2008).

* cited by examiner

IMPLANTABLE SELF-POWERED BIODEGRADABLE MEDICAL DEVICE TO TREAT OR PREVENT REPERFUSION INJURY

CROSS REFERENCE TO RELATED APPLICATION

The present application claims priority to U.S. provisional application Ser. No. 61/222,027 filed Jun. 30, 2009, the disclosure of which is incorporated herein by reference in its entirety.

TECHNICAL FIELD

The present invention relates to medical devices and methods for preventing and/or treating reperfusion injury.

BACKGROUND

Blockage of arteries, such as the coronary arteries, can result in reduced blood flow to the downstream tissue, such as the heart muscle. In the case of the coronary arteries, such a blockage can lead to acute myocardial infarction or heart attack. Various treatments have been proposed to restore blood flow to the affected area, e.g., the ischemic myocardium. This process of restoring blood flow to the affected area is known as reperfusion.

Treatments that have been proposed to restore blood flow include thrombolytic therapy, percutaneous coronary intervention (PCI) and bypass surgery. Thrombolytic therapy involves the administration of therapeutic agents to open the blockage. Some thrombolytic agents that have been proposed or used include streptokinase, urokinase, and alteplase (recombinant tissue plasminogen activator, rtPA).

Percutaneous coronary intervention involves delivering a treatment device to the affected area of the blood vessel to open the blocked site. Commonly, an angioplasty procedure is performed in which a balloon catheter is tracked through the vasculature, and, once the balloon is at the constriction, the balloon is expanded to open the blockage. Often a stent is expanded and left at the site to help maintain the patency of the vessel.

Coronary artery bypass surgery involves a graft vessel being taken from the patient and implanted to bypass the area of blockage. Blood then is allowed to flow around the blockage through the bypass graft.

Reperfusion of blood flow to the ischemic tissue, while beneficial, can at times result in damage to the tissue. Because the affected tissue has been deprived of oxygen and nutrients, the restoration of blood flow can result in inflammation and oxidative damage. This is known as reperfusion injury.

Some techniques have been proposed to prevent or reduce reperfusion injury. For example, glisodin has been proposed as a therapeutic treatment. However, there continues to be a need for improved techniques to prevent or treat reperfusion injury.

SUMMARY

In one embodiment, the present disclosure provides a biodegradable, self-powered medical device for preventing or reducing reperfusion injury, comprising a galvanic cell, the galvanic cell comprising: a first biodegradable electrode member; and a second biodegradable electrode member comprising a biodegradable conductive polymer and an electrode-releasable therapeutic agent, wherein the galvanic cell generates an electric force sufficient to cause the electrode-releasable therapeutic agent to be released from the biodegradable conductive polymer and elute to a target location. The electrode-releasable therapeutic agent may be a scavenger for reactive oxygen species, such as ascorbate anions. The galvanic cell may be used to provide prolonged release of therapeutic agent to protect against reactive oxygen species produced on reperfusion.

In certain embodiments, the medical device may additionally comprise a reservoir material containing a burst-release therapeutic agent, which may also be a scavenger for reactive oxygen species, such as ascorbic acid. The medical device may additionally or alternatively comprise a biodegradable member coated with dimethylthiourea.

In another embodiment, the present disclosure provides a method of preventing or reducing reperfusion injury, comprising: administering to a subject a biodegradable, self-powered medical device, the medical device comprising a galvanic cell, the galvanic cell comprising: a first biodegradable electrode member; and a second biodegradable electrode member comprising a biodegradable conductive polymer and an electrode-releasable therapeutic agent, and allowing the galvanic cell to generate an electric force sufficient to cause the electrode-releasable therapeutic agent to be released from the biodegradable conductive polymer region and elute to a target location. The method may include implanting the medical device in an area susceptible to reperfusion injury.

DETAILED DESCRIPTION

Figure 1:
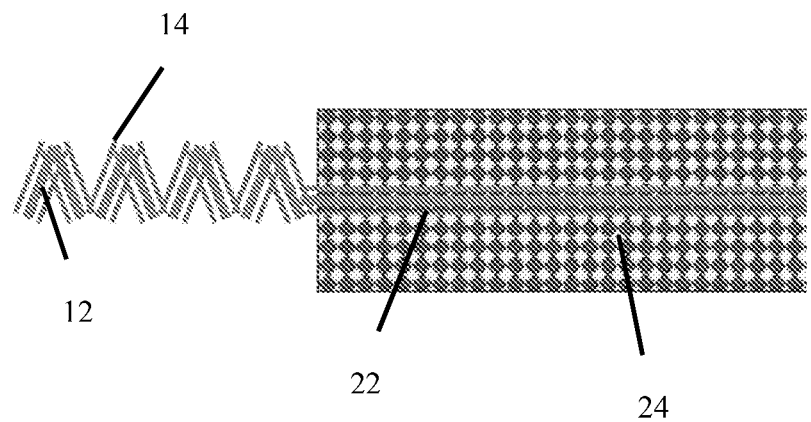
FIG. 1 shows a biodegradable, self-powered medical device for preventing or reducing reperfusion injury in accordance with an embodiment of the present disclosure.

FIG. 1 shows a biodegradable, self-powered medical device for preventing or reducing reperfusion injury in accordance with an embodiment of the present disclosure. The medical device comprises a first biodegradable electrode member 12 coated with a reservoir 14 comprising a reservoir material containing a first therapeutic agent; and a second biodegradable electrode member 24 comprising a biodegradable conductive polymer and a second therapeutic agent. As depicted in FIG. 1, the second biodegradable electrode member 24 is coated on an internal biodegradable member 22. As described further below, the first biodegradable electrode member 12 and the second biodegradable electrode member 24 form a galvanic cell that generates an electric force sufficient to cause the second therapeutic agent to be released from the biodegradable conductive polymer and elute to a target location.

The first biodegradable electrode member 12 may be made of a number of suitable biodegradable materials, as long as the first biodegradable electrode member 12 is capable of forming a galvanic cell with the biodegradable conductive polymer, which acts as the second biodegradable electrode member 24. For example, in certain embodiments, the first biodegradable electrode member 12 may be made of magnesium, iron, calcium, zinc, manganese, and/or suitable alloys, such as magnesium alloys or iron alloys, or composites of these materials. In one example, the first biodegradable electrode member 12 is made of magnesium, an agent known to reduce free oxygen radicals. The first biodegradable electrode member 12 may be of any suitable size and shape. For example, the first biodegradable electrode member 12 may be a micro-helix to provide a greater surface area and/or to provide a means for anchoring the medical device in tissue.

The reservoir 14 may comprise a biodegradable porous ceramic suitable for containing a therapeutic agent. The biodegradable porous ceramic may be, for example, magnesium oxide, magnesium hydroxide, iron oxide and/or calcium phosphate. The first therapeutic agent may be dispersed in the biodegradable porous ceramic. In certain embodiments, the first therapeutic agent may be a reactive oxygen species scavenger, such as ascorbic acid. The porous structure of the biodegradable ceramic improves the efficiency of drug delivery. In certain embodiments, the biodegradable porous ceramic filled with a reactive oxygen species scavenger provides an immediate burst of a reactive oxygen metabolite scavenger, protecting the tissue against the large amount of free oxygen radicals generated during the acute phase of reperfusion. In this way, the first therapeutic agent serves as a burst-release therapeutic agent that is released from the reservoir upon, or shortly after, implantation. The release rate of the first therapeutic agent may be adjusted by altering the nanostructure of the biodegradable porous ceramic.

The second biodegradable electrode member 24 may comprise a biodegradable conductive polymer and a second therapeutic agent. As depicted in FIG. 1, the second biodegradable electrode member 24 is coated on an internal biodegradable member 22. In certain embodiments, for example, the internal biodegradable member 22 may be made of magnesium, iron, calcium, zinc, manganese and/or suitable alloys, such as magnesium alloys or iron alloys, or composites of these materials. In one example, the internal biodegradable member 22 is made of magnesium, an agent known to reduce free oxygen radicals.

The biodegradable conductive polymer may be prepared by a number of suitable methods. For example, a biodegradable conductive polypyrrole-poly(D,L-lactide) may be prepared through emulsion polymerization of pyrrole (PPy) in a poly(D,L-lactide) (PDLLA) solution in chloroform, as described in Z. Wang, et al., *A Biodegradable Electrical Bioconductor Made of Polypyrrole Nanoparticle/Poly(D, L-Lactide) Composite: a Preliminary in vitro Biostability Study*, J. Biomed. Mater. Res. 66A: 738-746 (2003), which is incorporated herein by reference. Non-limiting examples of the biodegradable conductive polymers that may be used in accordance with embodiments of the present disclosure include polypyrrole and its derivatives, polyaniline and its derivatives, polythiophene and its derivatives, poly(p-phenylene vinylene) and its derivatives, polysulfone and its derivatives, polyacetylene and its derivatives, poly (3,4-ethylenedioxythophene) and its derivatives, poly(ethylene oxide) (PEO) and its derivatives, poly(D,L-lactide) and its derivatives, poly-ε-caprolactone, a cyanoethylpullulan polymer, polypyrrole-poly(D,L-lactide), polypyrrole-polylactic-polyglycolic acid (PPy-PLGA), and combinations thereof. For example, the biodegradable conductive polymer may comprise PPy-PLGA. It is known that the biodegradable, water soluble polypyrrole coating can also act as a scavenger for reactive oxygen species.

The second therapeutic agent contained by the second biodegradable electrode member 24 may comprise a charged therapeutic agent. Non-limiting examples of suitable charged therapeutic agents include a therapeutic agent that is inherently charged, a therapeutic agent that is covalently attached to a charged molecule, a therapeutic agent that is non-covalently coupled to a charged molecule, a therapeutic agent that is attached to or encapsulated within a charged particle, and/or a combination thereof. In certain embodiments, the charged therapeutic agent may comprise a scavenger for reactive oxygen species, such as ascorbate anion. In certain embodiments, the second therapeutic agent may comprise more than one charged therapeutic agent. For example, a cocktail of charged therapeutic agents may be used.

The second therapeutic agent may be dispersed in the biodegradable conductive polymer in any of a number of suitable ways. For example, a polypyrrole coating may be prepared by electropolymerization in the presence of the charged therapeutic agent to be incorporated into the polypyrrole.

A biodegradable, self-powered medical device as shown in FIG. 1 and in accordance with certain embodiments of the disclosure may be used to treat or reduce reperfusion injury. Tissue ischemia and the decrease of oxygen intake by the cells result in accumulation of hypoxanthine and the conversion of xanthine dehydrogenase into xanthine oxidase. During reperfusion, the accumulated hypoxanthine is converted by the xanthine oxidase in the presence of molecular oxygen ($O_2$) into xanthine and free radicals of oxygen: superoxides, peroxides and hydroxyl. These reactive oxygen species cause an inflammatory process characterized by the increase in endothelial permeability to fluids, macromolecules and inflammatory cells, potentially causing reperfusion injury to the tissue. Scavengers for reactive oxygen species, such as methylene blue, ascorbic acid and ascorbate anions, suppress the production of free oxygen radicals by competing with $O_2$ for the electrons from xanthine oxidase, and thus may be used for preventing or reducing reperfusion injury.

In an example of using a device such as that shown in FIG. 1, the device is implanted in tissue susceptible to reperfusion injury. The burst-release therapeutic agent then elutes from the reservoir 14 that coats the first biodegradable electrode member 12, providing an immediate burst of a reactive oxygen metabolite scavenger, thereby protecting the tissue against the large amount of free oxygen radicals generated during the acute phase of reperfusion. In the example wherein the first biodegradable electrode member 12 comprises magnesium and the reservoir 14 comprises a biodegradable porous ceramic coating, the biodegradable porous ceramic coating does not provide corrosion protection for the magnesium, so the magnesium will start corroding once exposed to an electrolyte, for example, blood.

The magnesium of the first biodegradable electrode member 12 serves as an electrode for a galvanic cell with the second biodegradable electrode member 24. The galvanic cell further enhances magnesium corrosion. The galvanic coupling also results in the second biodegradable electrode member 24, e.g., polypyrrole, acting as a cathode and becoming negatively charged. Because the second biodegradable electrode member 24 in this example is doped with negatively charged electrode-releasable therapeutic agent, e.g., ascorbate anions, the negative charge of the second biodegradable electrode member 24 will cause the negatively charged electrode-releasable therapeutic agent to be released to the target area. The negatively charged electrode-releasable therapeutic agent, e.g., ascorbate anions, can serve to provide further protection against reactive oxygen species. Moreover, the biodegradable, water soluble polypyrrole may also act as a scavenger for reactive oxygen species. In this way, the device maintains a sufficient level of protection against low levels of reactive oxygen species produced during the subsequent hours after reperfusion.

Due to the design of the device, corrosion and/or biodegradation, the internal biodegradable member 22 will also be or become exposed to biological tissues or fluids. Depending upon the design, over time the internal biodegradable member 22, e.g., comprising an electrode made of magnesium, may also serve as an electrode for a galvanic cell with the second biodegradable electrode member 24. In this example, the galvanic cell will enhance magnesium corrosion of the internal biodegradable member 22 and will further facilitate release of the electrode-releasable therapeutic agent.

As evident from the therapeutic agent release operation described above, a medical device such as that shown in FIG. 1 can be used to effectively prevent or reduce reperfusion injury caused by reactive oxygen species and can have both acute and prolonged effects. Thus, the device can be capable of delivering rapidly a therapeutic agent into myocardial cells to counter the burst of oxygen free radicals generated early in reperfusion and providing an extended release of a therapeutic agent and maintaining sufficient myocardial levels to protect against low levels of reactive oxygen species produced during the subsequent hours.

As is also evident from the operation described above, the medical device is self-powered because the galvanic coupling, dissolution and drug release occur due to the components of the device and their interaction. The device does not require any separate power source or electric circuit. Such a drug delivery device is simpler in design and more convenient to use than typical devices requiring a separate power source or electric circuit, due to minimum interference with the daily activities of the subject into which the device is implanted. Furthermore, every component of the delivery device can be biodegradable, providing the additional advantage of avoiding the undesirable side effects (e.g., chronic inflammation) associated with non-biodegradable materials that remain in the body of the subject for a long time, e.g., for a period of years.

Figure 2:
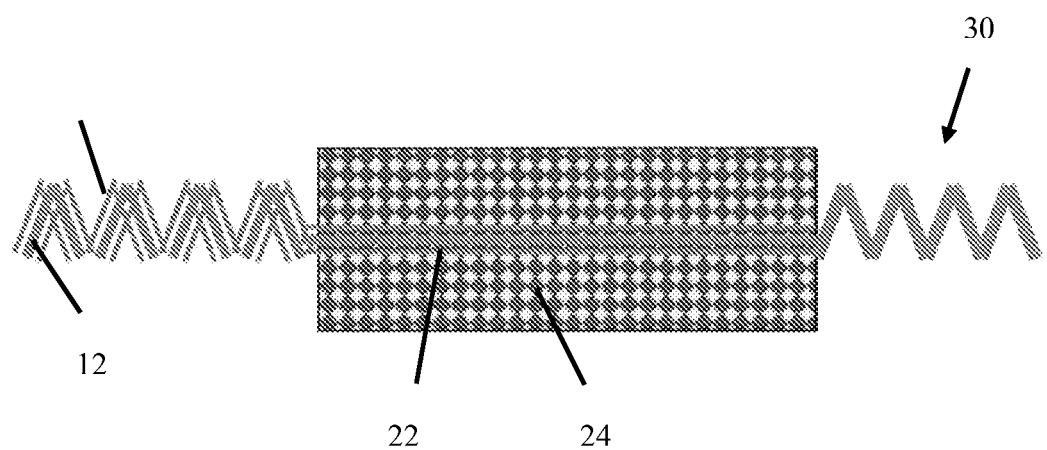
FIG. 2 shows a biodegradable, self-powered medical device for preventing or reducing reperfusion injury in accordance with another embodiment of the present disclosure.

The medical device may further comprise a means for fixing the medical device in a target tissue. For example, the first biodegradable electrode member 12 and/or another part of the device may be formed as a helix and/or with barbs to facilitate implantation into and/or affixation to tissue. Other means of fixing may be used such as adhesives, hooks, spurs and the like. In addition, as shown in FIG. 2, a further micro-helix 30 may be used to fix the medical device into the target tissue. In certain embodiments, the micro-helix 30 may further comprise a coating of an adsorbed, self-assembled layer of a therapeutic agent, which may be prepared by any of a number of suitable methods known in the art. For example, the chemical or electrochemical formation of an adsorbed, self-assembled layer of thiourea and substituted thiourea is described in A. E. Bolzan, et al., *Electrochemical Study of Thiourea and Substituted Thiourea Adsorbates on Polycrystalline Platinum Electrodes in Aqueous Sulfuric Acid*, Journal of Applied Electrochemistry 32: 611-620 (2002), which is incorporated herein by reference. In certain embodiments, the absorbed, self-assembled layer may comprise dimethylthiourea, an inhibitor of magnesium corrosion and an effective scavenger of reactive oxygen species with a long half-life.

In the embodiment of FIG. 2, in the example of a micro-helix 30 comprising a magnesium helix coated with dimethylthiourea, because the dimethylthiourea inhibits magnesium corrosion and also acts as an effective scavenger of reactive oxygen species, this design further provides prolonged protection against reperfusion injury. Magnesium itself can also be beneficial in reducing free radicals; thus, the inhibited corrosion can further serve to provide the device with prolonged protection against reperfusion injury.

The biodegradable, self-powered medical device of the present disclosure may be any suitable size. Also, the device may be any suitable shape, such as a patch, helix, ring, etc.

The biodegradable, self-powered medical device in accordance with the present disclosure may be implanted or otherwise used in body structures, cavities, or lumens such as the vasculature, gastrointestinal tract, abdomen, peritoneum, airways, esophagus, trachea, colon, rectum, biliary tract, urinary tract, prostate, brain, spine, lung, liver, heart, skeletal muscle, kidney, bladder, intestines, stomach, pancreas, ovary, uterus, cartilage, eye, bone, joints, and the like.

The biodegradable, self-powered medical device may be administered in a number of suitable ways. For example, the device may be administered intravascularly, such as inside the coronary artery. The device may also be implanted in a heart chamber or in heart tissue or placed on the outer surface of the heart in a region susceptible to reperfusion injury. Similar procedures can be used to deliver a therapeutic agent to ischemic tissues other than in the heart, for example in the brain.

In certain embodiments, the biodegradable, self-powered medical device may further comprise, as described above, a means for fixing the device in a target tissue. For example, as mentioned above, a micro-helix may be used to actively fix the device into the target tissue. This may be carried out in any of a number of suitable ways. For example, the medical device may be administered to a patient with the micro-helix in the shape of a coil, which then expands and inserts itself into the target tissue, such as the vascular wall. One may also twist and push the micro-helix into the target tissue. Alternatively, the micro-helix may be pushed straight into the tissue.

While the above examples have been described with respect to the delivery of therapeutic agents that act as scavengers for reactive oxygen species, other therapeutic agents may also be used. Exemplary non-genetic therapeutic agents include anti-thrombogenic agents such heparin, heparin derivatives, prostaglandin (including micellar prostaglandin E1), urokinase, and PPack (dextrophenylalanine proline arginine chloromethylketone); anti-proliferative agents or anti-restenosis agents such as enoxaparin, angiopeptin, paclitaxel, sirolimus (rapamycin), tacrolimus, everolimus, zotarolimus, monoclonal antibodies capable of blocking smooth muscle cell proliferation, hirudin, and acetylsalicylic acid; anti-inflammatory agents such as dexamethasone, rosiglitazone, prednisolone, corticosterone, budesonide, estrogen, estrodiol, sulfasalazine, acetylsalicylic acid, mycophenolic acid, and mesalamine; anti-neoplastic/anti-proliferative/anti-mitotic agents such as paclitaxel, epothilone, cladribine, 5-fluorouracil, methotrexate, doxorubicin, daunorubicin, cyclosporine, cisplatin, vinblastine, vincristine, epothilones, endostatin, trapidil, halofuginone, and angiostatin; anti-cancer agents such as antisense inhibitors of c-myconcogene; anti-microbial agents such as triclosan, cephalosporins, aminoglycosides, nitrofurantoin, silver ions, compounds, or salts; biofilm synthesis inhibitors such as non-steroidal anti-inflammatory agents and chelating agents such as ethylenediaminetetraacetic acid, O,O'-bis (2-aminoethyl)ethyleneglycol-N,N,N',N'-tetraacetic acid and mixtures thereof; antibiotics such as gentamycin, rifampin, minocyclin, and ciprofloxacin; antibodies including chimeric antibodies and antibody fragments; anesthetic agents such as lidocaine, bupivacaine, and ropivacaine; nitric oxide; nitric oxide (NO) donors such as linsidomine, molsidomine, L-arginine, NO-carbohydrate adducts, polymeric or oligomeric NO adducts; anti-coagulants such as D-Phe-Pro-Arg chloromethyl ketone, an RGD peptide-containing compound, heparin, antithrombin compounds, platelet receptor antagonists, anti-thrombin antibodies, anti-platelet receptor antibodies, enoxaparin, hirudin, warfarin sodium, Dicumarol, aspirin, prostaglandin inhibitors, platelet aggregation inhibitors such as cilostazol and tick antiplatelet factors; vascular cell growth promotors such as growth factors, transcriptional activators, and translational promotors; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; agents which interfere with endogenous vascoactive mechanisms; inhibitors of heat shock proteins such as geldanamycin; angiotensin converting enzyme (ACE) inhibitors; beta-blockers; βAR kinase (βARK) inhibitors; phospholamban inhibitors; protein-bound particle drugs such as ABRAXANE®; structural protein (e.g., collagen) cross-link breakers such as alagebrium (ALT-711); and any combinations and prodrugs of the above.

Exemplary biomolecules include peptides, polypeptides and proteins; oligonucleotides; nucleic acids such as double or single stranded DNA (including naked and cDNA), RNA, antisense nucleic acids such as antisense DNA and RNA, small interfering RNA (siRNA), and ribozymes; genes; carbohydrates; angiogenic factors including growth factors; cell cycle inhibitors; and anti-restenosis agents. Nucleic acids may be incorporated into delivery systems such as, for example, vectors (including viral vectors), plasmids or liposomes.

Non-limiting examples of proteins include serca-2 protein, monocyte chemoattractant proteins (MCP-1) and bone morphogenic proteins ("BMP's") such as, for example, BMP-2, BMP-3, BMP-4, BMP-5, BMP-6 (VGR-1), BMP-7 (OP-1), BMP-8, BMP-9, BMP-10, BMP-11, BMP-12, BMP-13, BMP-14 or BMP-15. Preferred BMP's are any of BMP-2, BMP-3, BMP-4, BMP-5, BMP-6 and BMP-7. These BMPs can be provided as homodimers, heterodimers, or combinations thereof, alone or together with other molecules. Alternatively, or in addition, molecules capable of inducing an upstream or downstream effect of a BMP can be provided. Such molecules include any of the "hedgehog" proteins, or the DNA's encoding them. Non-limiting examples of genes include survival genes that protect against cell death, such as anti-apoptotic Bcl-2 family factors and Akt kinase; serca 2 gene; and combinations thereof. Non-limiting examples of angiogenic factors include acidic and basic fibroblast growth factors, vascular endothelial growth factor, epidermal growth factor, transforming growth factors α and β, platelet-derived endothelial growth factor, platelet-derived growth factor, tumor necrosis factor α, hepatocyte growth factor, and insulin-like growth factor. A non-limiting example of a cell cycle inhibitor is a cathespin D (CD) inhibitor. Non-limiting examples of anti-restenosis agents include p15, p16, p18, p19, p21, p27, p53, p57, Rb, nFkB and E2F decoys, thymidine kinase and combinations thereof, and other agents useful for interfering with cell proliferation.

Exemplary small molecules include hormones, nucleotides, amino acids, sugars, and lipids and compounds having a molecular weight of less than 100 kD.

Exemplary cells include stem cells, progenitor cells, endothelial cells, adult cardiomyocytes, and smooth muscle cells. Cells can be of human origin (autologous or allogenic) or from an animal source (xenogenic), or can be genetically engineered. Non-limiting examples of cells include side population (SP) cells, lineage negative (Lin$^-$) cells including Lin$^-$CD34$^-$, Lin$^-$CD34$^+$, Lin$^-$cKit$^+$, mesenchymal stem cells including mesenchymal stem cells with 5-aza, cord blood cells, cardiac or other tissue derived stem cells, whole bone marrow, bone marrow mononuclear cells, endothelial progenitor cells, skeletal myoblasts or satellite cells, muscle derived cells, go cells, endothelial cells, adult cardiomyocytes, fibroblasts, smooth muscle cells, adult cardiac fibroblasts +5-aza, genetically modified cells, tissue engineered grafts, MyoD scar fibroblasts, pacing cells, embryonic stem cell clones, embryonic stem cells, fetal or neonatal cells, immunologically masked cells, and teratoma derived cells. Any of the therapeutic agents may be combined to the extent such combination is biologically compatible.

The foregoing description and examples have been set forth merely to illustrate the invention and are not intended to be limiting. Each of the disclosed aspects and embodiments of the present invention may be considered individually or in combination with other aspects, embodiments, and variations of the invention. Modifications of the disclosed embodiments incorporating the spirit and substance of the invention may occur to persons skilled in the art and such modifications are within the scope of the present invention.

What is claimed is:

1. A biodegradable, self-powered medical device for preventing or reducing reperfusion injury, comprising:
   a galvanic cell comprising:
      a first biodegradable electrode member; and
      a second biodegradable electrode member comprising a biodegradable conductive polymer and an electrode-releasable therapeutic agent dispersed in the biodegradable conductive polymer;
   wherein the galvanic cell generates an electric force sufficient to cause the electrode-releasable therapeutic agent to be released from the biodegradable conductive polymer and elute to a target location.

2. The medical device according to claim 1, wherein the first biodegradable electrode member comprises at least one of magnesium, iron, calcium, zinc, manganese, a magnesium alloy, an iron alloy and a composite comprising at least one these materials.

3. The medical device according to claim 1, wherein the medical device further comprises a reservoir material containing a burst-release therapeutic agent.

4. The medical device according to claim 3, wherein the reservoir material containing the burst-release therapeutic agent comprises a biodegradable porous ceramic.

5. The medical device according to claim 4, wherein the biodegradable porous ceramic is selected from the group consisting of magnesium oxide, magnesium hydroxide, iron oxide, and calcium phosphate.

6. The medical device according to claim 3, wherein the burst-release therapeutic agent is a scavenger for reactive oxygen species.

7. The medical device according to claim 3, wherein the burst-release therapeutic agent is ascorbic acid.

8. The medical device according to claim 1, wherein the second biodegradable electrode member is coated on an internal biodegradable member comprising at least one of magnesium, iron, calcium, zinc, manganese, a magnesium alloy, an iron alloy and a composite comprising at least one these materials.

9. The medical device according to claim 1, wherein the biodegradable conductive polymer is selected from the group consisting of polypyrrole and its derivatives, polyaniline and its derivatives, polythiophene and its derivatives, poly(p-phenylene vinylene) and its derivatives, polysulfone and its derivatives, polyacetylene and its derivatives, poly (3,4-ethylenedioxythophene) and its derivatives, poly(ethylene oxide) (PEO) and its derivatives, poly(D,L-lactide) and its derivatives, poly-ϵ-caprolactone, a cyanoethylpullulan polymer, polypyrrole-poly(D,L-lactide), polypyrrole-polylactic-polyglycolic acid (PPy-PLGA), and combinations thereof.

10. The medical device according to claim 1, wherein the electrode-releasable therapeutic agent is a scavenger for reactive oxygen species.

11. The medical device according to claim 10, wherein the electrode-releasable therapeutic agent is ascorbate anion.

12. The medical device according to claim 1, further comprising a means for fixing the medical device in a target tissue.

13. The medical device according to claim 1, wherein the medical device further comprises a biodegradable member coated with dimethylthiourea.

14. The medical device according to claim 1, wherein the first biodegradable electrode member is coated with a reservoir material containing a burst-release therapeutic agent.

15. The medical device according to claim 14, wherein the first biodegradable electrode member comprises at least one of magnesium, iron, calcium, zinc, manganese, a magnesium alloy, an iron alloy and a composite comprising at least one these materials.

16. The medical device according to claim 14, wherein the burst-release therapeutic agent is a scavenger for reactive oxygen species.

17. A biodegradable, self-powered medical device for preventing or reducing reperfusion injury, comprising:
    a first biodegradable electrode member; and
    a second biodegradable electrode member comprising a biodegradable conductive polymer and an electrode-releasable therapeutic agent dispersed in the biodegradable conductive polymer;
    wherein the first biodegradable electrode member and the second biodegradable electrode member are adapted to form a galvanic cell that generates an electric force sufficient to cause the electrode-releasable therapeutic agent to be released from the biodegradable conductive polymer and elute to a target location.

18. A method of preventing or reducing reperfusion injury, comprising:
    administering to a subject a biodegradable, self-powered medical device, the medical device comprising:
    a galvanic cell comprising:
        a first biodegradable electrode member; and
        a second biodegradable electrode member comprising a biodegradable conductive polymer and an electrode-releasable therapeutic agent dispersed in the biodegradable conductive polymer; and
    allowing the galvanic cell to generate an electric force sufficient to cause the electrode-releasable therapeutic agent to be released from the biodegradable conductive polymer and elute to a target location.

19. The method according to claim 18, wherein the step of administering the medical device comprises implanting the medical device in an area susceptible to reperfusion injury.

20. The method according to claim 18, wherein the medical device further comprises a reservoir material containing a burst-release therapeutic agent.

* * * * *